United States Patent [19]
Grimm et al.

[11] Patent Number: 5,229,109
[45] Date of Patent: Jul. 20, 1993

[54] LOW TOXICITY INTERLEUKIN-2 ANALOGUES FOR USE IN IMMUNOTHERAPY

[75] Inventors: Elizabeth A. Grimm; Keith Heaton, both of Houston, Tex.

[73] Assignee: Board of Regents, The University of Texas System, Austin, Tex.

[21] Appl. No.: 868,765

[22] Filed: Apr. 14, 1992

[51] Int. Cl.$^5$ .............................................. A61K 45/05
[52] U.S. Cl. .................................. 424/85.2; 424/85.1
[58] Field of Search ............................ 424/85.2, 85.1

[56] References Cited

U.S. PATENT DOCUMENTS

| | | | |
|---|---|---|---|
| 4,690,915 | 9/1987 | Rosenberg | 424/85.2 |
| 4,863,740 | 9/1989 | Kissel et al. | 424/85.1 |
| 4,999,339 | 3/1991 | Paradise et al. | 424/85.2 |
| 5,037,644 | 8/1991 | Shaked et al. | 424/85.2 |
| 5,066,489 | 11/1991 | Paradise et al. | 530/351 |
| 5,098,702 | 3/1992 | Zimmerman et al. | 424/85.21 |
| 5,102,872 | 4/1992 | Singh et al. | 514/21 |

OTHER PUBLICATIONS

L. Collins et al., "Identification of Specific Residues of Human Interleukin 2 That Affect Binding to the 70-kDa Subunit (p70) of the Interleukin 2 Receptor," *Proceedings of the National Academy of Science USA*, 85:7709–7713, 1988.

Grace Ju et al., "Structure-Function Analysis of Human Interleukin-2, Identification of Amino Acid Residues Required for Biological Activity," *The Journal of Biological Chemistry*, 262(12):5723–5731, 1987.

Steven A. Rosenberg, M. D., Ph.D. et al., "Experience with the Use of High-Dose Interleukin-2 in the Treatment of 652 Cancer Patients,"*Annals of Surgery*, 210:474–485, 1989, Abstract Only.

K. Sauvé et al., "Localization in Human Interleukin 2 of the Binding Site to the α Chain (p55) of the Interleukin 2 Receptor," *Proceedings of the National Academy of Science USA*, 88:4636–4640, 1991.

Ulrich Weigel et al., "Mutant Proteins of Human Interleukin 2," *European Journal of Biochemistry*, 180:295–300, 1989.

M. P. Weir et al., "Structure-Activity Relationships of Recombinant Human Interleukin 2," *Biochemistry*, 27:6883–6892, 1988.

Sandra M. Zurawski et al., "Mouse Interleukin-2 Structure-Function Studies: Substitutions in the First α-Helix Can Specifically Inactivate p70 Receptor Binding and Mutations in the Fifth α-Helix Can Specifically Inactivate p55 Receptor Binding," *The EMBO Journal*, 8(9):2583–2590, 1989.

Grant et al., "The Interleukin 2 Receptor (IL-2R): The IL-2R α Subunit Alters the Function of the IL-2R β Subunit to Enhance IL-2 Binding and Signaling by Mechanisms That Do Not Require Binding of IL-2 to IL-2R α Subunit," *Proc. Natl. Acad. Sci. USA*, 89:2165–2169, 1992.

Landgraf et al., "Conformational Perturbation of Interleukin-2: A Strategy for the Design of Cytokine Analogs," *Proteins: Structure, Function, and Genetics*, 9:207–216 (1991).

Boone et al., "Interleukin-2 Analogs," *Dev. Biol. Stand.*, 69:157–168, 1988, abstract only.

*Primary Examiner*—Michael G. Wityshyn
*Assistant Examiner*—Choon Koh
*Attorney, Agent, or Firm*—Arnold, White & Durkee

[57] ABSTRACT

The properties of two recombinant human IL-2 analogues with mutations at Arginine 38 (→Alanine) and Phenylalanine 42 (→Lysine) were analyzed and compared to those of native IL-2. These analogues were found to maintain their ability to bind to the intermediate IL-2 receptor, p75, while binding only minimally to the high affinity p55+p75 receptor complex. The analogues also maintained the ability to stimulate peripheral blood mononuclear cells to generate lymphokine activated killing (LAK). However, IL-1β and TNF-α secretion were significantly reduced in response to the analogues, as compared to the native IL-2 molecule. These analogues are therefore potentially valuable low-toxicity alternatives to IL-2 in human immunotherapy and adoptive immunotherapy treatment strategies.

17 Claims, 4 Drawing Sheets

LOW TOXICITY INTERLEUKIN-2 ANALOGUES FOR USE IN IMMUNOTHERAPY

The government owns rights in the present invention pursuant to grant number CA 45225 the National Institute of Health.

BACKGROUND OF THE INVENTION

1. Field of the Invention

The present invention relates generally to the fields of immunotherapy and cancer treatment. The invention is directed to the identification and selection of cytokines with low toxicity, and to the use of increased dosages of such cytokines in clinical treatment strategies and anticancer therapy. In particular, the beneficial use of low toxicity interleukin-2 analogues which maintain their tumoricidal effects is disclosed. The invention further concerns the use of such low toxicity interleukin-2 analogues in adoptive immunotherapy.

2. Description of the Related Art

Human interleukin 2 (IL-2) is a potent immunoregulatory cytokine, first described as a lymphokine capable of promoting the long term proliferation of activated T cells in vitro (Morgan et al., 1976; Ruscetti et al., 1977). Subsequently, IL-2 has also been shown to modulate various other immune functions, including exerting effects on cytotoxic T cells (Gillis et al., 1980), natural killer cells (Ortaldo et al., 1984), activated B cells (Mingari et al., 1984) and lymphokine activated killer (LAK) cells (Grimm et al., 1982; Mazumder & Rosenberg, 1984).

A CDNA encoding human IL-2 has been cloned (Taniguchi et al., 1983), and the primary protein sequence deduced. In eukaryotic cells, IL-2 is synthesized as a precursor polypeptide of 153 amino acids, from which 20 amino acids are removed to generate mature secreted IL-2. Using molecular biological techniques, active recombinant human IL-2 has been produced in *E. coli* (Rosenberg et al., 1984), in insect cells (Smith et al., 1985), and in mammalian COS cells (Taniguchi et al., 1983).

The biological effects of IL-2 are mediated through binding to specific receptors on the surface of target cells. At least three different forms of IL-2 receptors (IL-2Rs) are known: the low affinity ($K_d = 10-30$ nM); intermediate affinity ($K_d = 0.8-2$ nM); and high affinity ($K_d = 10-50$ pM) receptors (Waldmann et al., 1989). The low affinity IL-2R is a polypeptide chain of $M_r \sim 55$ kD, termed p55 or IL-2R$\alpha$ (Leonard et al., 1984; Nikaido et al., 1984; Cosman et al., 1984), whereas the intermediate affinity IL-2R is a polypeptide chain of $M_r \sim 70-75$ kD, termed p75 or IL-2R$\beta$ (Hatakeyama et al., 1989). A complex formed between p55 and p75, with additional components, corresponds to the high-affinity IL-2R (Hatakeyama et al., 1989; Herrmann & Diamantstein, 1988).

The biological functions of each of these receptors have been investigated by studying the effects of IL-2 binding to cells expressing natural, or recombinant, receptors. It has been shown that IL-2 activates lymphokine activated killing (LAK) via the intermediate affinity IL-2 receptor molecule p75, and not via the high affinity p55+p75 complex.

In recent years, the administration of IL-2 has proven to be of some benefit in cancer therapy, and particularly in the treatment of certain patients with renal cell carcinoma. Currently around 20% of renal cancer patients exhibit signs of tumor regression when treated with the optimal tolerable dosage of IL-2. However, the clinical usefulness of IL-2 immunotherapy is currently limited due to problems of marked toxicity. The toxicity associated with IL-2 treatment in humans is such that only 10% or less of the optimal dose, as derived from animal studies, can be tolerated. Unfortunately, therefore, the "curative doses" achieved in animal models cannot be approached in human patients.

Furthermore, even at the doses currently used, symptoms of toxicity, including for example, malaise, nausea and vomiting, diarrhoea, fluid retention, hypotension, and even organ dysfunction, are often observed in patients undergoing IL-2 therapy (Rosenberg et al., 1989). Moreover, and particularly concerning, IL-2 treatment can sometimes lead to the death of the patient, with the mortality rate attributable to IL-2 toxicity in one treatment study being 1.5% (Rosenberg et al., 1989).

One of the key mechanisms of IL-2-induced tumor rejection in cancer patients is believed to be the induction of lymphokine activated killing (LAK). LAK cells have been shown to be extremely potent tumoricidal lymphocytes. In contrast, the detrimental toxic side effects are believed to result from the elaboration of secondary cytokines such as interleukin-1s (IL-1s) and tumor necrosis factors (TNFs).

The generation of a cytokine which has reduced toxicity towards human cells would lead to the development of more effective methods of clinical immunotherapy. In particular, the identification of less toxic cytokines which can nonetheless induce LAK would be important in the development of new therapeutic anticancer strategies with wide ranging applications. The identification of an IL-2 variant with such properties would be particularly advantageous in that it would allow the development of a broader therapeutic window for IL-2 treatment and allow established clinical IL-2 doses to be increased to curative levels known to be effective in animal tumor models.

SUMMARY OF THE INVENTION

The present invention seeks to overcome one or more of these or other drawbacks inherent in the prior art by providing methods for human immunotherapy with reduced toxic side effects. The invention relates to the identification and selection of cytokines with low toxicity, and more particularly, to the use of increased dosages of such cytokines in clinical immunotherapy and cancer treatment. In particular, the present invention concerns the beneficial use of low toxicity interleukin-2 (IL-2) analogues which maintain their tumoricidal effects. Further aspects of the invention relate to the use of low toxicity interleukin-2 analogues in generating activated cells for use in adoptive immunotherapy.

A key aspect of the present invention is the discovery that certain human IL-2 analogues, in particular those which are specific for the intermediate affinity IL-2 receptor, maintain their tumoricidal activities whilst exhibiting reduced toxicity. Such IL-2 analogues are therefore "low-toxicity IL-2 analogues", which is a term used herein to refer to an IL-2 analogue or mutant with amino acid sequence differences from native IL-2, which analogue induces less secondary cytokine production than native IL-2. Secondary cytokines are molecules such as interleukin-1s (IL-1s) and tumor necrosis factors (TNFs), and include, for example, IL-1$\beta$, TNF$\alpha$, TNF$\beta$, and IFN-$\gamma$.

It is contemplated that preferred low-toxicity IL-2 analogues for use in accordance with the present invention will be human IL-2 analogues which exhibit substantial binding to the intermediate affinity IL-2 receptor but which do not exhibit substantial binding to the high affinity IL-2 receptor. The IL-2 receptors referred to herein are those established in the art, for example, see Waldmann (1989). As such, the intermediate affinity IL-2 receptor is a polypeptide of $M_r \sim 70$–75 kD, herein termed p75. The high affinity IL-2 receptor is a complex containing, amongst other components, p75 and a polypeptide of $M_r \sim 50$–55 kD (termed p55), the receptor being termed the p55+p75 complex.

Low-toxicity IL-2 analogues can therefore also be defined as analogues which have a mutated, or otherwise altered, p55 binding site. The important region for p55 binding is believed to reside generally within residues 30–60 of the IL-2 molecule, and more particularly within the B α-helix formed by residues 33–46 (Sauvé et al., 1991). Even more particularly, the residues Lysine 35, Arginine 38, Phenylalanine 42, and Lysine 43, are believed to play an important role in this interaction (Sauvé et al., 1991). It is therefore contemplated that IL-2 analogues with mutations or modifications within these areas, or of these particular residues, may prove to be low toxicity IL-2 analogues suitable for use in accordance herewith.

The term "substantial binding" is used to indicate that IL-2 or an IL-2 analogue binds to, or otherwise functionally interacts with, a given receptor polypeptide. It is contemplated that IL-2 analogues for use in the present invention will bind substantially to the intermediate, but not to the high, affinity IL-2 receptor. As such, they will bind to the intermediate affinity IL-2 receptor in essentially the same way as native IL-2. In contrast, it is believed that useful analogues will exhibit in the order of between about 1% and about 25%, and preferably, of between about 2% and about 10%, binding to the high affinity receptor, as compared to native IL-2.

The toxicity of IL-2 or an IL-2 analogue is preferably determined by measuring the release of secondary cytokines from lymphocytes in response to stimulation by the IL-2 molecule. This can be achieved by measuring the amounts of various cytokines produced, for example, IL-1β, TNFα, TNFβ, and IFN-γ, by any appropriate method, such as by ELISA or radioimmunoassay. An important aspect of the present invention is the inventors, discovery that the use of lymphocyte-containing samples from fresh human blood is particularly advantageous for conducting such assays. It is believed that both the human source and the newly-isolated nature of such lymphocytes is important as this mirrors the clinical situation most closely. Accordingly, it is therefore believed to be preferable to use fresh human peripheral blood mononuclear cells or lymphocytes (PBMC or PBL, respectively) to analyze the cytokine-inducing activity of an IL-2 analogue.

IL-2 analogues for use in the present invention will exhibit lower cytokine inducing activity than native IL-2. In preferred embodiments, it is contemplated that they will exhibit a reduction of between about 25% and about 70%, and preferably, of between about 40% and about 75%, as compared to the native molecule.

It is further contemplated that IL-2 analogues for use in the present invention will maintain their ability to stimulate lymphokine activated killing (LAK) as this is believed to be one of the effective clinical mechanisms underlying IL-2 therapy. The ability to stimulate lymphokine activated killing is herein defined as the ability of a lymphokine, such as an IL-2 analogue, to induce lymphocytes into an activated state so that they become lymphokine activated "killer cells" and are able to lyse tumor cells. The capability to induce LAK is believed to be a resultant property of binding to the intermediate affinity IL-2 receptor.

By means of assays employing PBMC- or PBL-, the inventors' discovered that two human IL-2 analogues, R38A and F42K (Hoffman La-Roche), are suitable for use in the present invention. R38A is an arginine to alanine mutant at amino acid position 38 of the IL-2 sequence, and F42K is a phenylalanine to lysine mutant at amino acid position 42. To generate R38A or F42K, one would perform site specific mutagenesis on the native IL-2 sequence, such as on the human IL-2 sequence disclosed in U.S. Pat. No. 4,992,367, incorporated herein by reference. The preferred method for preparing R38A or F42K, as described herein, is that developed by Sauvé and colleagues (Sauvé et al., 1991; Collins et al., 1988; Ju et al., 1987; each incorporated herein by reference).

To generate IL-2 analogue(s) such as these, one would obtain a cDNA encoding IL-2, preferably human IL-2, and engineer an amino acid change in the protein by specifically mutating the DNA sequence which encodes the IL-2 protein. One would achieve this by analyzing the protein and DNA sequences, and designing an oligonucleotide containing a specific altered codon, which oligonucleotide could then be exchanged with the corresponding native portion of the DNA sequence. After confirming the nucleotide change, for example, by sequencing, the altered DNA could be used to direct the expression of the IL-2 analogue in a recombinant prokaryotic or eukaryotic host cell, and the IL-2 analogue could then be purified.

It is contemplated that other analogues or mutants may be generated which also have low toxicity and will therefore be useful in accordance with the present invention. To accomplish this one could simply create a novel IL-2 analogue, for example, by site-specific mutagenesis, and then determine whether the analogue meets the criteria for a low toxicity analogue set forth herein. That is, one would test its ability to bind substantially to the intermediate, but not to the high, affinity IL-2 receptor; to induce LAK; and to exhibit reduced secondary cytokine inducing activity. Such techniques of producing protein variants or mutants by site specific mutagenesis of the encoding DNA sequence will be known to those of skill in the art.

Alternatively, it is even possible that chemically modified IL-2 variants will exhibit the desirable low toxicity properties. As the shape and properties of the amino acid side group substituents determine, in part, the interactive capacity of a polypeptide, it is contemplated that methods of altering the side chain group, other than replacing it by genetic engineering, may also be useful. Any of the numerous chemical modification methods known to those of skill in the art could therefore be employed to generate an IL-2 analogue, which could be routinely tested for advantageous properties as disclosed herein.

As discussed above, analogues which have a mutated, or otherwise altered, p55 binding site may prove to be useful low-toxicity IL-2 analogues. It is therefore contemplated that one may particularly wish to create an IL-2 analogue, by either genetic engineering or chemical modification, which has a mutation(s) located within residues 30–60, and more preferably, within residues 33–46 which constitute the B α-helix, and even more preferably, within any one of residues 35, 38, 42, or 43.

IL-2 may be prepared from various sources and by different methods, as disclosed in numerous U.S. patents. These include, for example, the preparation of IL-2 from T cells, such as from hybrid murine T cell lines or malignant human T cell lines, as disclosed in U.S. Pat. Nos. 4,407,945 and 4,473,642, and 4,401,756, respectively, all of which are incorporated herein by reference. Alternatively, expression of IL-2 in mammalian cells and its preparation could be achieved by following the methods disclosed in U.S. Pat. No. 4,992,367, incorporated herein by reference.

In certain embodiments the present invention provides a method for stimulating the immune system of an animal, which method comprises administering to the animal a therapeutically effective amount of a low-toxicity interleukin-2 analogue in a pharmacologically acceptable form. Preferred IL-2 analogues for use in such a method are the IL-2 analogues R38A and F42K, as methods for their preparation are clearly established. However, as discussed above, it is contemplated that any IL-2 analogue that meets the low toxicity criteria may be used.

It is contemplated that such stimulation of the immune system by low toxicity IL-2 analogues will have particular utility in the treatment of human cancer, and even more particularly, in the treatment of human renal cell carcinoma or melanoma. Low toxicity IL-2 analogues will thus have utility in human therapy in much the same way as native IL-2 does, but with the distinct advantage of being able to be administered at higher doses.

Various methods are considered to be appropriate for the administration of the IL-2 analogues to human subjects. Of course, they may be administered in a therapeutically effective amount in any suitable pharmaceutical composition, such as is currently used for native IL-2 therapy. However, the maximum therapeutic dose of an analogue may be increased from those used for the native compound. A particularly suitable stable pharmaceutical composition is considered to be that described in U.S. Pat. No. 5,037,644, incorporated herein by reference, developed for the parenteral administration of IL-2. Alternatively, the IL-2 analogues could be administered in a slow-release form, for example, as a liposome formation, or encapsulated within a biodegradable polymer matrix, as disclosed in U.S. Pat. Nos. 4,863,740, and 4,832,686, respectively, each incorporated herein by reference.

If desired, IL-2 analogue compositions could also be administered in combination with effective doses of other therapeutic agents. For example, with DTIC, in the treatment of patients with malignant melanoma, as disclosed in U.S. Pat. Nos. 4,999,339, and 5,066,489, incorporated herein by reference; or with flavone-8-acetic acid, in the treatment of patients with renal carcinoma, as disclosed in U.S. Pat. No. 5,061,488, incorporated herein by reference. Also, they could be used in conjunction with an immunotoxin that binds selectively to human tumor cells, as described in U.S. Pat. No. 4,894,227, incorporated herein by reference.

The IL-2 analogues could be given daily by continuous infusion or given on alternative days, perhaps with other immunotherapeutic agents being administered on the other day. Doses of the IL-2 analogues would be increased relative to the doses of native IL-2. As the doses are increased they should, of course, be closely monitored to determine if toxic side effects appeared at a particular increased dose. Such clinical and experimental analyses are well known to those of skill in the art, and would, for example, have been used to establish the current doses of native IL-2 used in therapy.

In addition to use in direct infusion therapy, it is further contemplated that the IL-2 analogues will also have utility in adoptive immunotherapy. Adoptive immunotherapy is an approach to treating cancer in which immune cells with antitumor reactivity, with or without other compounds, are transferred to a tumor-bearing patient. A particular approach to adoptive immunotherapy using IL-2 and lymphokine activated killing (LAK) cells, has been described in U.S. Pat. No. 4,690,915, incorporated herein by reference. This technique is proposed to be equally suitable for use with the low toxicity IL-2 analogues disclosed herein.

Further embodiments of the present invention therefore concern improved methods for the ex vivo preparation of lymphokine activated killer (LAK) cells and their use in adoptive immunotherapy. To prepare LAK cells in this manner one would incubate a composition comprising lymphocytes histocompatible with the lymphocytes of the animal to be treated ex vivo in the presence of a low-toxicity IL-2 analogue. One may then use such LAK cells to stimulate the immune system of the animal, for example, as a method of treating cancer, by administering to the animal a therapeutically effective amount of the LAK cells.

In preferred embodiments for conducting adoptive immunotherapy it is contemplated that the composition comprising histocompatible lymphocytes would be a composition containing peripheral blood mononuclear cells obtained from the animal to be treated. One would then incubate these cells with the IL-2 analogue, and preferably with R38A or F42K, for a period of time sufficient to allow stimulation, such as, for example, for three to four days. Then one may wish to test the ability of the cells to lyse fresh tumor cells, but not normal cells, i.e., to confirm the presence of LAK activity. Next, one would infuse the LAK cells into the animal or patient from which the blood sample was taken, in other words, into the autologous animal or patient. If desired, it is also contemplated that one could additionally administer the IL-2 analogue itself to the animal or patient during this period.

DETAILED DESCRIPTION OF THE PREFERRED EMBODIMENTS

Figure 1:
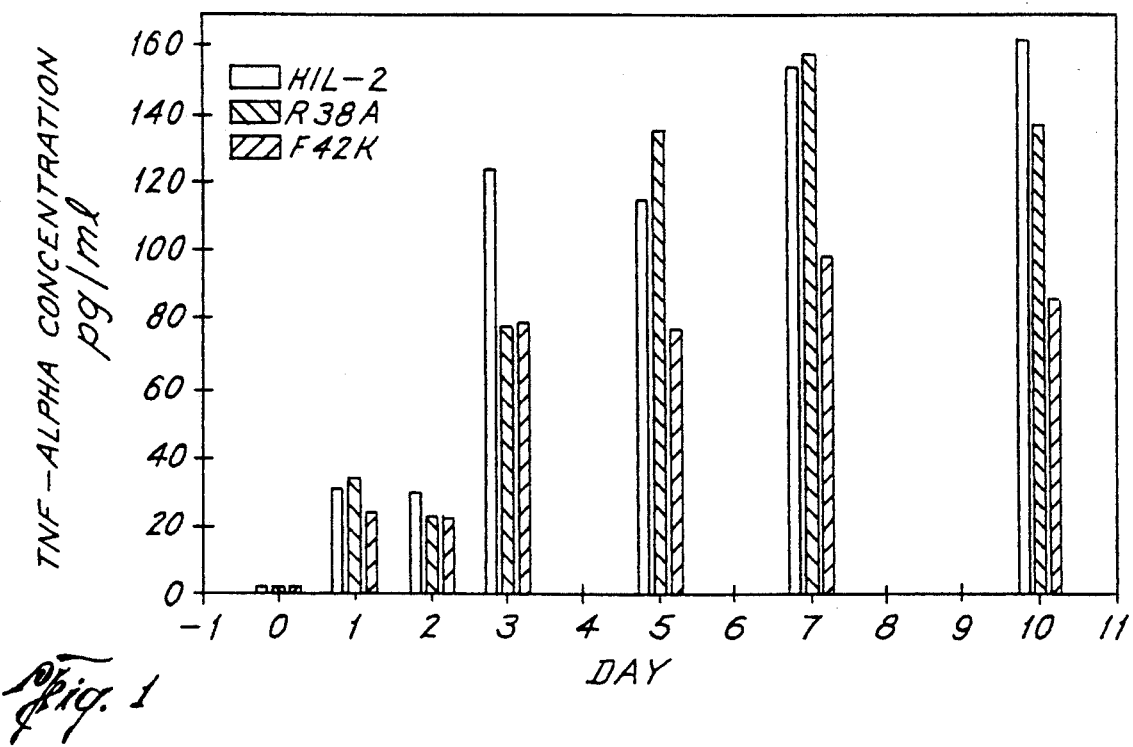
FIG. 1. TNF-α Production by PBMC in Response to native IL-2 and the IL-2 analogues R38A and F42K. Experiment 1.
Figure 2:
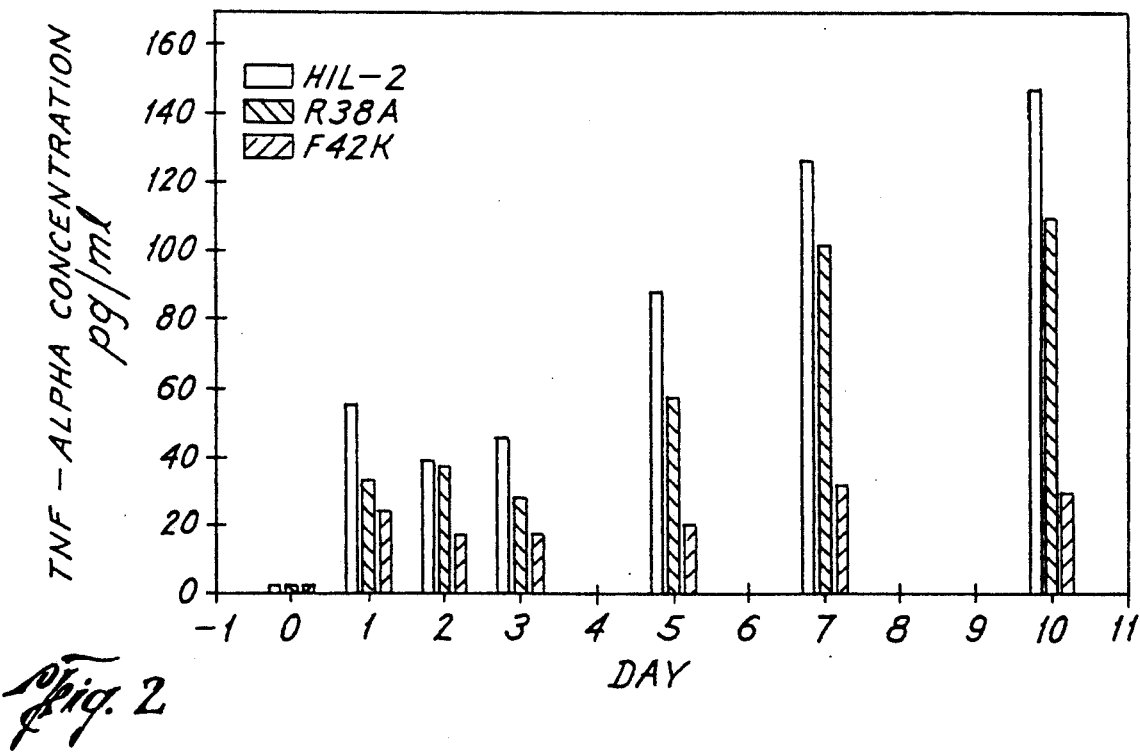
FIG. 2. TNF-α Production by PBMC in Response to native IL-2 and the IL-2 analogues R38A and F42K. Experiment 2.
Figure 3:
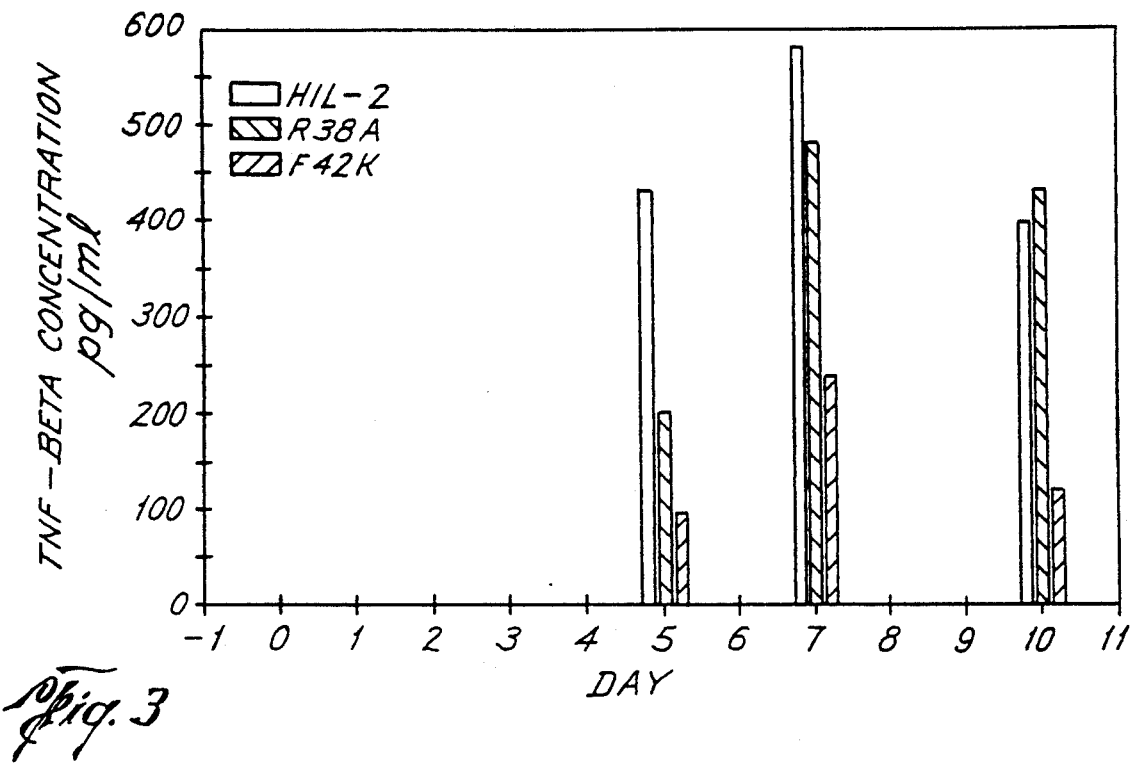
FIG. 3. TNF-β Production by PBMC in Response to native IL-2 and the IL-2 analogues R38A and F42K. Experiment 1.
Figure 4:
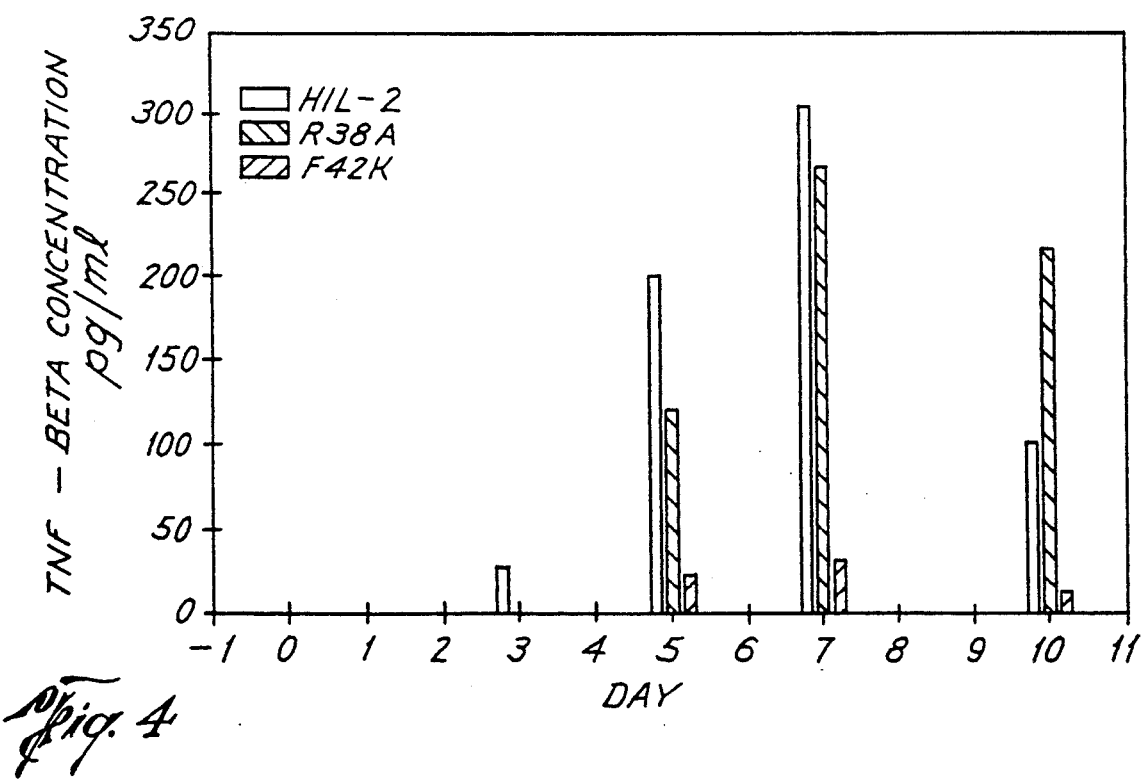
FIG. 4. TNF-β Production by PBMC in Response to native IL-2 and the IL-2 analogues R38A and F42K. Experiment 2.
Figure 5:
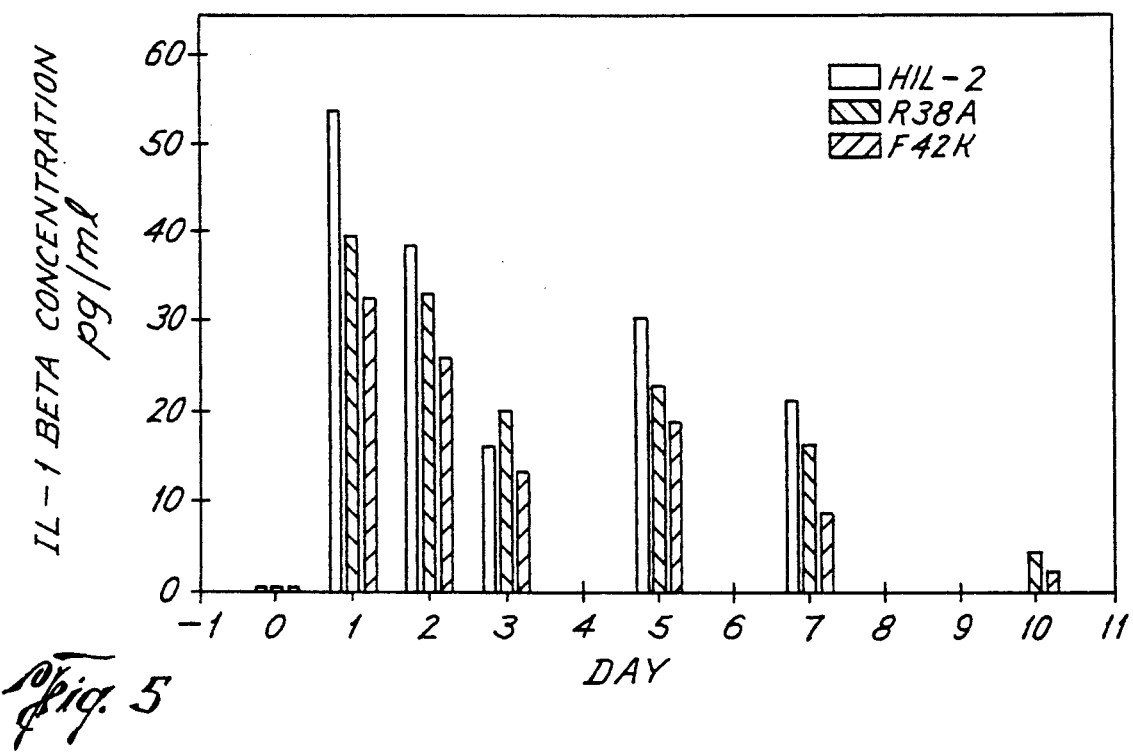
FIG. 5. IL-1β Production by PBMC in Response to native IL-2 and the IL-2 analogues R38A and F42K. Experiment 1, 35 minutes.
Figure 6:
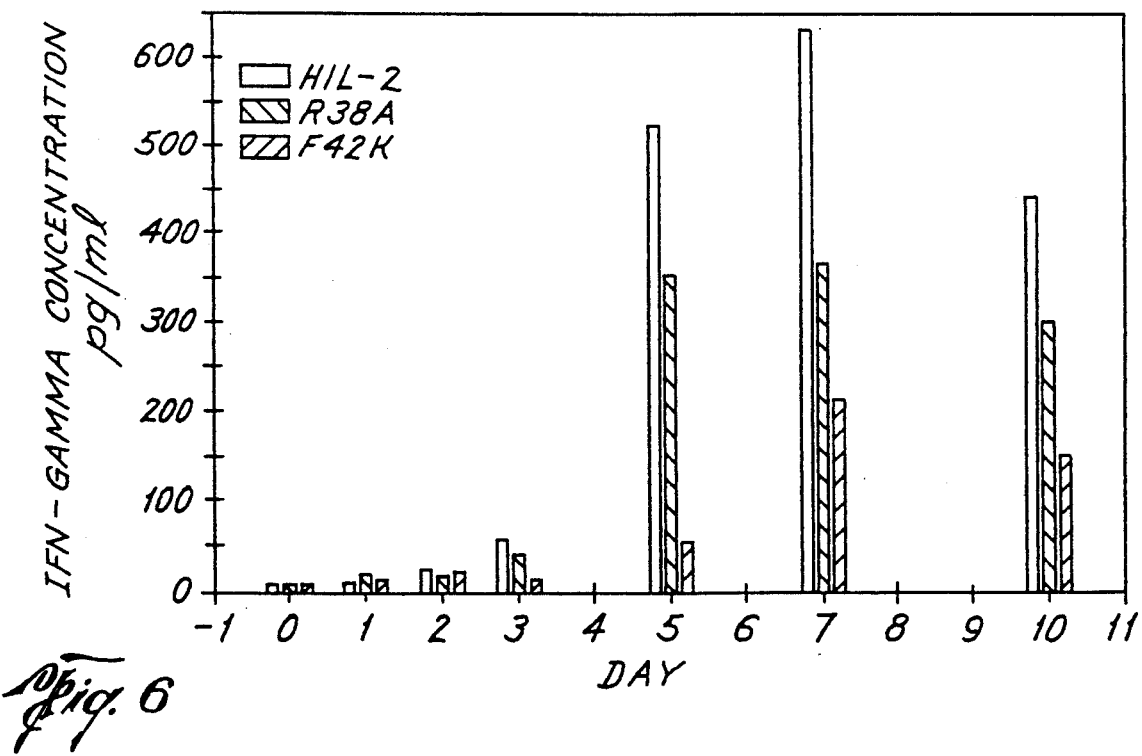
FIG. 6. IFN-γ Production by PBMC in Response to native IL-2 and the IL-2 analogues R38A and F42K. Experiment 1.
Figure 7:
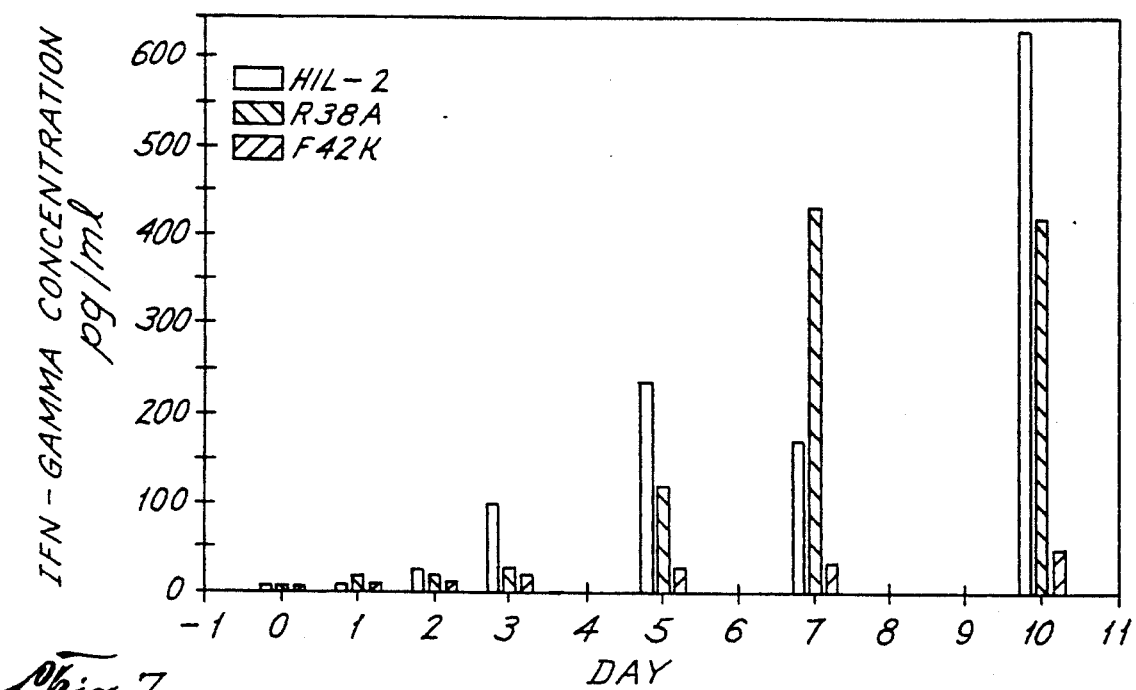
FIG. 7. IFN-γ Production by PBMC in Response to native IL-2 and the IL-2 analogues R38A and F42K. Experiment 2.

Interleukin 2 (IL-2) is a cytokine which stimulates the immune system and which exerts its biological effects following binding to specific receptors on the surface of target cells. IL-2 has many biological effects, for example, it is known to induce the stimulation of activated B and T cells (including cytotoxic T cells), natural killer (NK) cells, and lymphokine activated killer (LAK) cells. Recombinant human IL-2 can be generated as described in U.S. Pat. Nos. 4,992,367, 4,407,945, 4,473,642, and 4,401,756, all of which are incorporated herein by reference.

IL-2 has been used with some success clinically in the treatment of renal cell carcinoma and melanoma, and further clinical uses are currently under investigation, such as in the general normalization of immune functions. However, human IL-2 therapy has a major problem—that of toxicity. The adverse toxic side effects associated with IL-2 therapy are due to the elaboration of secondary cytokines such as interleukin-1s (IL-1s) and tumor necrosis factors (TNFs), for example, IL-1β and TNF-α. IL-1s and TNFs are well-known for inducing dramatic hemodynamic changes resulting in the fluid shifts and hypotension which are the major limitations to IL-2 use in humans. This toxicity means that the "curative" doses achieved in animal models cannot be approached in humans, which tolerate only 10% or less of the optimal dose delineated in animal studies.

The induction of lymphokine-activated killing (LAK) is one of the mechanisms proposed to be operating in the tumor rejection observed in cancer patients undergoing IL-2 therapy. Indeed, LAK are extremely potent tumoricidal lymphocytes. In both human and animal systems, it is known that IL-2 activates LAK via the intermediate affinity IL-2 receptor molecule, p75, and not via the high affinity p55+p75 complex.

The identification of an IL-2 variant or mutant which maintains its LAK-inducing abilities, but which has less associated toxicity, would be particularly useful in the clinical setting. In light of the information discussed above, the inventors reasoned that identification of an IL-2 analogue which binds to the intermediate, but not the high, affinity IL-2 receptor may provide such a low toxicity molecule.

The interaction between IL-2 and IL-2 receptors has been investigated by using genetic engineering to map sites in IL-2 that interact with different receptor polypeptides. For example, Asp-20 in the NH2 terminus of IL-2 has been determined to control binding to the intermediate-affinity IL-2 receptor, p75 (Collins et al., 1988). A cluster of specific amino acids that form the binding site in IL-2 for the low-affinity IL-2 receptor, p55, has also been identified (Sauvé et al., 1991). In such studies, it was demonstrated that IL-2 molecules with mutations at Arginine 38 (→Alanine) or Phenylalanine 42 (→Lysine) could no longer bind to the low affinity receptor p55, but maintained their affinity for the intermediate receptor p75 (Sauvé et al., 1991).

The present inventors investigated the capacities of the Arg→Ala and Phe→Lys IL-2 mutants described by Sauvé et al. (1991) to induce LAK in the absence of proliferation, and to stimulate the production of the secondary cytokines IL-1s, TNFs, and IFN-γ. These studies lead to the elucidation of previously-unknown advantageous properties of the IL-2 analogues. As disclosed hereinbelow, in studies using fresh human peripheral blood mononuclear cells or lymphocytes (PBMC or PBL, respectively), the inventors found that these IL-2 analogues could activate human LAK with significantly less secondary cytokine release. As the secondary cytokines pose the major toxicity problem in clinical treatment, this is a particularly important finding.

Findings such as these have not been reported previously. Indeed, no studies have been documented which revealed any differences in secondary cytokine production or release caused by these IL-2 analogues, as compared to that observed with native IL-2. In this regard, the inventors' choice of fresh human PBMC or PBL is believed to be particularly important as such human cells represent exactly the cell types that will be involved in the clinical response.

The IL-2 analogues may be administered in therapeutically effective amounts in any suitable pharmaceutical composition, for example, those currently used for native IL-2 therapy. They could also be administered in slow-release form, for example, as a liposome formation, or encapsulated within a biodegradable polymer matrix, as disclosed in U.S. Pat. Nos. 4,863,740, and 4,832,686, respectively, each incorporated herein by reference.

If desired, IL-2 analogue treatment could be combined with other therapies, such as radiotherapy, chemotherapy, surgery, or with the administration of other therapeutic agents, or even with immunotoxins. In addition to use in direct infusion therapy, it is contemplated that the IL-2 analogues will also be useful in adoptive immunotherapy. They could be used to stimulate patients' cells to an activated state in vitro, and the activated cells could be re-administered to the same patient to add a further dimension to the body's disease fighting capabilities.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Preparation of p75-Specific Human IL-2 Analogues

1. Molecular Biological Techniques

IL-2 analogue proteins were prepared in *E. coli* using site-specific mutagenesis, as described hereinbelow, and also in Sauvé et al. (1991); Collins et al. (1988); and Ju et al. (1987); each incorporated herein by reference. The following method is believed to be appropriate for the preparation of any IL-2 analogue using site-specific mutagenesis. Naturally, the specific IL-2 analogue prepared will depend on the choice of residue to be modified and the design of an appropriate oligonucleotide.

It is contemplated that advantages will be found in the creation of an expression plasmid for the expression of IL-2 and IL-2 analogues, as described in Ju et al. (1987). IL-2 expression plasmids can be constructed, for example, from the low-copy-number-compatible plasmid pRK248cIts, which carries the gene for a temperature-sensitive repressor (Casadaban & Cohen, 1980). A cDNA insert coding for human IL-2 should be inserted into the plasmid, for example, following its released from pIL2-2B (Smith et al., 1985) by digestion with appropriate restriction enzymes, such as BamHI and AhaIII. It is considered to be advantageous for the cDNA encoding the mature IL-2 cDNA to be inserted into the plasmid such that it is downstream of the $P^L$ promoter and so that it disrupts a marker gene, for example, a tetracycline-resistance gene. This can be achieved using techniques of DNA manipulation, such as by employing restriction enzyme technology and blunt end ligation.

For in vitro mutagenesis, synthetic oligonucleotides should be prepared as described in Matteucci & Caruthers (1981). The oligonucleotides should be in the order of about 20 to about 30 nucleotides long and designed to encode specific amino acid substitutions, i.e., they should match the native DNA sequence except at the codon of the amino acid to be changed. For example, to change arginine at position 38 to alanine, one would change the codon corresponding to position 38 to specify alanine, i.e., change it to GCA, GCC, GCG. To change phenylalanine at position 42 to lysine, one would change the codon corresponding to position 42 to specify lysine, i.e., change it to AAA or AAG. It is also believed to be advantageous to create oligonucleotides which also include a novel restriction endonuclease cleavage site, which can be used to monitor the incorporation of the mutated sequence at the correct location in the IL-2 gene.

An appropriate site-specific mutagenesis procedure is considered to be a modification of the method described by Morinaga et al. (1984). The IL-2 -containing plasmid should be digested with a restriction endonuclease(s) to produce linear molecules and gapped molecules produced by digestion with different restriction endonuclease(s), chosen to facilitate insertion of a new oligonucleotide. The large fragments from such digestion should be purified on agarose minigels, and for each mutagenesis, the linear and gapped plasmid DNA should be mixed with 5'-phosphorylated synthetic oligonucleotide in a small volume (approximately 12.5 µl) of an appropriate buffer such as polymerase-ligase-buffer (0.1 M NaCl, 6.5 mM Tris-HCl, pH 7.5, 4.5 mM $MgCl_2$, 100 mM 2-mercaptoethanol). The sample should be heated to denature the plasmid molecules, for example, at 100° C. for 5 minutes. The reaction mix should then be slowly cooled, for example, by incubating at room temperature for 30 minutes, at 4° C. for 30 minutes, and at 0° C. for 10 minutes, to allow renaturation of the plasmid DNA, formation of heteroduplex molecules, and annealing of the oligonucleotide.

After renaturation, nucleotides should be added, for example, 1mM ATP and 500 µM each of dATP, dCTP, dGTP, and TTP, along with DNA polymerase Klenow fragment (approximately 3 units) and $T_4$DNA ligase (approximately 1 unit), and the reaction incubated, for example, at 15° C. for 2-3 hours. A sample of the ligation reaction should then be used for transformation (Maniatis et al., 1982, incorporated herein by reference) of competent E. coli cells, such as MC1061 (pRK248cIts) cells. Colonies containing mutated plasmids can be identified by hybridization with the 5'-$^{32}$P-labeled oligonucleotide. Plasmid DNA from positive colonies can then be prepared by the miniprep procedure (Birnboim & Doly, 1979) and used for a second round of transformation and screening. Plasmid DNA from positive secondary transformations can be analyzed for the presence of the predicted new restriction site encoded by the oligonucleotide to verify the correct location of the mutation.

It is contemplated that one would usually wish to confirm the new nucleotide sequence by performing sequence analysis, for example, using the dideoxy chain termination method as modified for double-stranded plasmids. To perform such an analysis, one would linearize plasmid DNA and mix it with a synthetic oligonucleotide primer in polymerase reaction buffer (6.6 mM Tris-HCl, pH 7.5, 6.6 mM MgCl2, 13 mM NaCl, 5 mM dithiothreitol). The sample should then be denatured by heating at 100° C. and then cooled at 0° C. for 5 minutes. To this reaction one should add 10 µCi, for example, of [α-$^{32}$P]dATP of approximately 400 Ci/mmol and 0.01 M dithiothreitol. The mixture should be divided into four aliquots, and the aliquots used for the four dideoxy chain termination reactions as described in Sanger et al., (1977).

2. Production and Purification of IL-2 Analogues

Bacterial cells containing the IL-2 analogue expression plasmids should be grown at 30° C. to early logarithmic phase ($OD_{600}=0.5$) in an appropriate medium, such as M9 medium (Maniatis et al., 1982). The cultures should then be induced by transfer to 42° C. for approximately 2 hours, until the $OD_{600}=1.0\pm0.1$. Samples of the cultures can then be pelleted by centrifugation, for example, at 12,000×g for 1 minute at 4° C. Extracts can be made from these cell pellets by vigorous vortexing and heating at 100° C. in Laemmli sample buffer (Laemmli, 1970).

The IL-2 analogues can be prepared by any one of the many methods known in the art for the preparation of unmodified IL-2. For example, by employing the method disclosed for human IL-2 production in U.S. Pat. No. 4,992,367, incorporated herein by reference. Alternatively, one may wish to utilize the method described by Smith et al. (1985). The analogues could also be purified by immunoaffinity chromatography using a monoclonal antibody that binds recombinant human IL-2, as described in Bailon et al. (1987). Examples of monoclonal antibodies specific for recombinant human IL-2 include 5B1 (Bailon et al., 1987) and the antibodies disclosed in U.S. Pat. Nos. 4,772,572; and R.E. 33252 (a reissue of U.S. Pat. No. 4,473,493), each incorporated herein by reference. If desired, one may analyze the IL-2 analogues by polyacrylamide gel electrophoresis in the presence of sodium dodecyl sulfate (SDS/PAGE), preferably using 15% polyacrylamide gels, as described by Laemmli (1970).

EXAMPLE II p75-Specific Human IL-2 Analogues Generate Lymphokine Activated Killing with Decreased Secondary Cytokine Secretion The following recombinant human IL-2 analogues, generated as described above, were obtained from Hoffmann-La Roche:

R38A—Arginine (R) at position 38→Alanine (A)
F42K—Phenylalanine (F) at position 42→Lysine (K)

1. Receptor Binding

The IL-2 specific binding assay was carried out essentially as described by Robb et al., (1981) with the modifications described as follows. To remove IL-2 present during cell culturing, cells were washed once by centrifugation (500×g, for 5 minutes) and resuspended in binding buffer (RPMI 1640, 1% bovine serum albumin (BSA), 25 mM Hepes, pH 7.2). The cells were then incubated for 1 hour at 37° C. and the washing procedure was repeated three times. Each assay contained approximately $6 \times 10^5$ cells and $\approx 40$ pM $^{125}$I-IL-2 (50 µCi/µg) in 0.15 ml of binding buffer. Nonspecific binding was determined by inclusion of 50 nM unlabeled human rIL-2 in the assay. Incubations were carried out in duplicate or triplicate for 20 minutes at 37° C. Cell-bound radioactivity was separated from unbound radioactivity as described (Kilian et al., 1986), and the specific binding was calculated.

These analogues R38A and F42K, made by point-specific mutation, were found to maintain their ability to bind IL-2 receptor p75 while binding minimally (10% and 2%, respectively) to the high affinity p55+p75 receptor complex.

2. Secondary Cytokine Production

Further properties of recombinant human IL-2 and the two human IL-2 analogues R38A and F42K were next analyzed. The abilities of the same concentrations of IL-2 and the analogues to stimulate peripheral blood mononuclear cells to secrete IL-1β and TNF-α in vitro were first compared. At 24 hour intervals up to 7 days, the LAK culture supernatants from the above-described experiment were collected and tested for IL-1β and TNF-α content using ELISA methodology. Commercially available ELISA kits were purchased from R & D Systems (TNF-α and TNF-β), Immunotech (IL-1α and IL-1β), and Endogen (IFN-γ). The ELISAs were performed according to the protocols supplied by the manufacturer.

Both IL-1β and TNF-α were significantly decreased ($p<0.05$, 3-way ANOVA) at all time points using analogue F42K compared to that produced in response to native IL-2. IL-1β secretion decreased up to 43% (F42K) and 28% (R38A), and TNF-α decreased as much as 77% (F42K) and 66% (R38A).

3. LAK Generation

The abilities of optimal concentrations of IL-2 and the analogues to stimulate peripheral blood mononuclear cells to generate lymphokine activated killing (LAK) in vitro were next compared.

Fresh peripheral blood mononuclear cells (PBMC) obtained from leukopharesis of normal human donors were isolated over a Ficoll-Hypaque gradient. These cells were placed into culture using the serum-free media AIM V (Gibco) supplemented with either 0.5 nM native recombinant IL-2 or 1 nM of either of the IL-2 mutants, R38A and F42K. Non-adherent cells were tested for cytotoxicity against Daudi targets by a 4 hour $^{51}$Cr release assay, with specific lysis being presented as the mean of triplicate values. Cell-free supernatants from 3 day PBMC cultures were analyzed by ELISA for cytokine content. This data is presented as the mean of duplicate values and is representative of two experiments performed.

The generation of LAK as determined by $^{51}$Cr cytotoxicity assay against Daudi targets was significant, yet slightly decreased, for both analogues compared to native IL-2, as shown below:

|  | % maximal specific lysis 100:1 effector:target ratio |
|---|---|
| native IL-2: | 62 |
| R38A: | 55 |
| F42K: | 54 |

Figure 8:
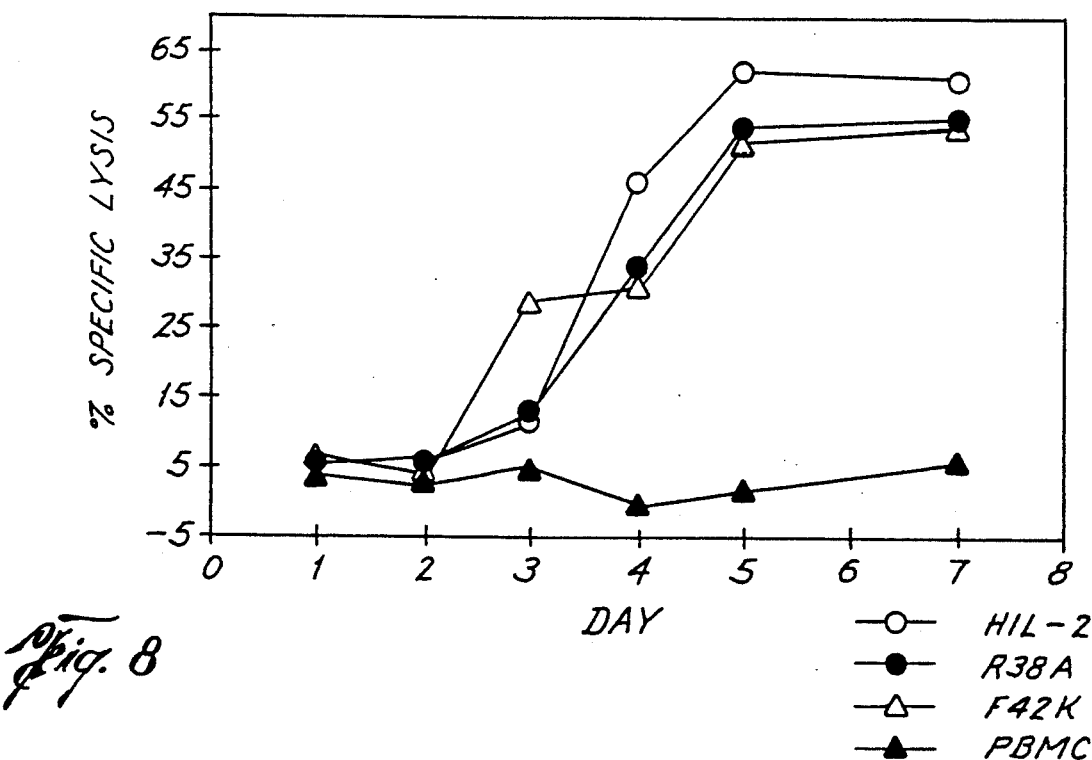
FIG. 8. Kinetics of LAK Generation.

The kinetics of LAK activation were also identical, with oncolytic activity first noted on day 3 and peaking on days 3-7 (FIG. 8).

4. FACS Analyses

Cultured PBMC were washed with PBS, 1% bovine serum albumin (BSA), and 0.1% sodium azide. To approximately one million cells, FITC-labelled monoclonal antibody against IL-2 receptor p55 or a non-specific control mouse IgG (Becton-Dickinson) was added. Following incubation for 30 minutes, the cells were washed twice using a Sorvall cell washer 2L, then fixed in PBS and 1% paraformaldehyde. The cells were then analyzed on Becton-Dickinson FACScan and results were presented as per cent of gated cells positive for p55 after subtraction of non-specific background fluorescence.

By FACS analysis the percentage of cells expressing p55 doubled (30% vs. 15%) in cultures stimulated for 72 hours by F42K but not R38A nor native IL-2 indicating differential shedding and/or internalization of the p55 receptor.

The data presented above indicate the potential of R38A and F42K IL-2 analogues as valuable alternatives to native IL-2 in immunotherapy regimens. The maintenance of LAK activity induction, coupled with the reduction in secondary cytokine production, show for the first time that these analogues would likely provide an effective, yet less toxic, means of cancer immunotherapy.

EXAMPLE III

Immunotherapy Protocols

The IL-2 analogues disclosed herein are believed to be of use in all of the human treatment regimens in which IL-2 is currently used. Moreover, the use of analogues such as R38A and F42K will represent a marked advancement in such treatment protocols as the doses may be increased without generating the toxic side effects currently observed with IL-2 treatment. It is contemplated that the IL-2 analogues will be useful in the treatment of various tumors, and in particular, in the treatment of patients with renal cell carcinoma or melanoma. They may also have utility in normalizing a subject's immune response, as described in U.S. Pat. No. 4,908,433, incorporated herein by reference.

For use in human treatment, the IL-2 analogues may be administered as pharmaceutical compositions exactly as native IL-2, but at increasing doses. If desired, IL-2 analogue compositions could be administered in combination with effective doses of other therapeutic agents. For example, with DTIC, for the treatment of malignant melanoma, as disclosed in U.S. Pat. Nos. 4,999,339, and 5,066,489, incorporated herein by reference; or with flavone-8-acetic acid, for the treatment renal carcinoma, as disclosed in U.S. Pat. No. 5,061,488, incorporated herein by reference.

Anti-tumor activity in humans could also be augmented by administering a pharmacologically effecrive amount of an IL-2 analogue and an immunotoxin that binds selectively to human tumor cells, as described in U.S. Pat. No. 4,894,227, incorporated herein by reference. It is believed that this would be particularly useful for the therapeutic treatment of ovarian and breast cancers and melanomas, where the number of selective tumor markers and specific immunotoxins is relatively large.

The IL-2 analogues could be given daily by continuous infusion or given on alternative days, perhaps with other immunotherapeutic agents been administered on the other day. Doses of the IL-2 analogues would be increased relative to the doses of native IL-2. As the doses are increased they should, of course, be closely monitored to determine if toxic side effects appeared at a particular increased dose. Such clinical and experimental analyses are well known to those of skill in the art, as exemplified by the establishmenr of the current doses used in IL-2 therapy.

It is contemplated that the IL-2 analogues could be combined with any of the pharmaceutical compositions currently known in the art in preparation for human administration. It is believed that advantages will be found in using the stable pharmaceutical compositions developed particularly for the parenteral administration of IL-2, as disclosed in U.S. Pat. No. 5,037,644, incorporated herein by reference. In such compositions, a therapeutically effective amount of IL-2 is dissolved in an aqueous, inert carrier medium comprising one or more biocompatible non-ionic polymeric detergents which act as solubilizers and/or stabilizers for IL-2. Suitable biocompatible non-ionic polymeric detergents include, for example, octylphenoxy polyethoxy ethanol compounds; polyethylene, glycol monostearate compounds; and polyoxyethylene sorbitan fatty acid esters.

Alternatively, IL-2 could be administered in a form designed for its slow release. For example, as a liposome formation with phospholipids and/or steroid lipids, as disclosed in U.S. Pat. No. 4,863,740, incorporated herein by reference. Or otherwise, formulated within a biocompatible, biodegradable polymer matrix, such as a collagen or albumin matrix, or a polymer or copolymer of lactic acid, lactide, glycolide or glutamic acid, as described in U.S. Pat. No. 4,832,686, incorporated herein by reference. In the latter case, the IL-2 slow release capsule could even be molded and implanted to fit a site from which malignant tissue had been removed.

In addition to use in direct infusion therapy, it is contemplated that the IL-2 analogues will also be useful in adoptive immunotherapy. Adoptive immunotherapy is an approach to treating cancer in which immune cells with antitumor reactivity are transferred to the tumor-bearing patient, see Rosenberg et al. (1977) and Rosenberg (1984). Native IL-2 has been shown to be a useful adjuvant to adoptive immunotherapy, wherein it is used to stimulate killer T-cell development (Rosenberg, 1985). Moreover, adoptive therapy utilizing IL-2 has demonstrated applicability in the treatment of a variety of advanced metastatic cancers in humans (Rosenberg et al., 1985).

Accordingly, it is submitted that the low toxicity IL-2 analogues, as disclosed herein, can be utilized in an adoptive immunotherapy protocol in a manner similar to the native molecule. The following protocols are contemplated to be of use in the utilizing IL-2 analogues in adoptive immunotherapy procedures.

A simplified approach may be taken thus: harvest fresh human peripheral blood mononuclear cells or lymphocytes (PBMC or PBL, respectively), for example, by cell separation using an IBM cell separator and accepted techniques. Next, incubate these cells overnight with the IL-2 analogues, and then slowly and continuously infuse the induced cells into the patients. Such therapy could initially be given 2 to 3 times a week. However, it could perhaps be given at more infrequent intervals stretched over a much longer period to time to ensure that infiltration into the tumor occurs.

A similar approach to adoptive immunotherapy for patients with cancer other than sarcoma has been described in more detail in U.S. Pat. No. 4,690,915, incorporated herein by reference. This technique uses human IL-2 and lymphokine activated killing (LAK) cells, and it is proposed that this methodology would be particularly appropriate for use with low toxicity IL-2 analogues. To perform such a method one would incubate peripheral blood mononuclear cells with the IL-2 analogue, for example, for three to four days. One would then test the ability of the resultant LAK cells to lyse fresh tumor cells, but not normal cells. The LAK cells would then be infused into the autologous patient, preferably, along with the intravenous administration of the analogue itself, every 8 hours, or so. It is further contemplated that patients may receive up to 90 doses of the IL-2 analogue and from 2.8 to $12.6 \times 10^{10}$ activated cells.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bailon et al., BioTechnology, 5:1195, 1987.
Birnboim & Doly, Nucleic Acids Res., 7:1513, 1979.
Casadaban & Cohen, J. Mol. Biol., 138:179, 1980.
Collins et al., Proc. Natl. Acad. Sci. U.S.A., 85:7709-7713, 1988.
Cosman et al., Nature, 312:768-771, 1984.
Gillis et al., J. Immunol., 124:1954, 1980.
Grimm et al., J. Exp. Med., 155:1823, 1982.
Hatakeyama et al., Science, 244:551-556, 1989.
Herrmann & Diamantstein, Eur. J. Immunol., 18:1051-1057, 1988.
Ju et al., J. Biol. Chem., 262:5723-5731, 1987.
Kilian et al., J. Immunol., 137:1538, 1986.
Laemmli, Nature, 227:680, 1970.
Leonard et al., Nature, 311:626-631, 1984.

Maniatis et al., Molecular Cloning, A Laboratory Manual, Cold Spring Harbour Laboratory, Cold Spring Harbour, N.Y.1982.
Matteucci & Caruthers, J. Am. Chem. Soc., 103:3185, 1981.
Mazumder & Rosenberg, J. Exp. Med., 159:495, 1984.
Mingari et al., Nature, 312:641, 1984.
Morgan et al., Science, 193:1007, 1976.
Morinaga et al., Bio/Technology, 636, 1984.
Nikaido et al., Nature, 311:631–635, 1984.
Ortaldo et al., J. Immunol., 133:779, 1984.
Robb et al., J. Exp. Med., 154:1455, 1981.
Rosenberg et al., Adv. Cancer Res., 25:323, 1977.
Rosenberg, Cancer Treat. Rep., 68:233, 1984.
Rosenberg et al., Science, 223:1412, 1984
Rosenberg, J. Natl. Cancer Inst., 75:595, 1985.
Rosenberg et al., N. Eng. J. Med., 313:1485, 1985.
Rosenberg et al., Ann. Surg., 210(4):474, 1989.
Ruscetti et al., J. Immunol., 119:131, 1977.
Sanger et al., Proc. Natl. Acad. Sci. U.S.A., 74:5463, 1977.
Sauvé et al., Proc. Natl. Acad. Sci. U.S.A., 88:4636, 1991.
Smith et al., Proc. Natl. Acad. Sci. U.S.A., 82:8404, 1985
Taniguchi et al., Nature, 302:305, 1983.
Waldmann, Annu. Rev. Biochem., 58:875–911, 1989.

What is claimed is:

1. A method for stimulating the immune system of an animal comprising administering to the animal a therapeutically effective amount of a low-toxicity interleukin-2 analogue, which low-toxicity interleukin-2 analogue exhibits reduced binding to the high affinity interleukin-2 receptor as compared to native interleukin-2, in a pharmacologically acceptable form.

2. The method of claim 1, wherein the low-toxicity interleukin-2 analogue exhibits substantial binding to the intermediate affinity interleukin-2 receptor but does not exhibit substantial binding to the high affinity interleukin-2 receptor.

3. The method of claim 1, wherein the low-toxicity interleukin-2 analogue has an amino acid substitution or modification within the B α-helix formed by residues 33–46.

4. The method of claim 3, wherein the low-toxicity interleukin-2 analogue is R38A.

5. The method of claim 3, wherein the low-toxicity interleukin-2 analogue is F42K.

6. The method of claim 1, wherein the low-toxicity interleukin-2 analogue is administered to the animal parenterally.

7. The method of claim 1, wherein the low-toxicity interleukin-2 analogue is administered to the animal encapsulated within a biodegradable polymer or slow-release capsule.

8. The method of claim 1, wherein the low-toxicity interleukin-2 analogue is administered to the animal within a liposome formulation.

9. The method of claim 1, wherein the low-toxicity interleukin-2 analogue is administered to the animal in an amount of between about 1000 U/kg/day to about 100,000,000 U/kg/day.

10. The method of claim 1, further defined as a method for treating cancer.

11. The method of claim 10, wherein the cancer to be treated is renal cell cancer or melanoma.

12. A method in accordance with any one of claims 1 or 10, wherein the animal is a human patient.

13. An improved method for preparing lymphokine activated killer cells for use in adoptive immunotherapy of an animal, wherein the improvement comprises incubating a composition comprising lymphocytes histocompatible with the lymphocytes of the animal to be treated ex vivo in the presence of a low-toxicity interleukin-2 analogue.

14. The method of claim 13, wherein the low-toxicity interleukin-2 analogue has an amino acid substitution or modification within the B α-helix formed by residues 33–46.

15. The method of claim 14, wherein the low-toxicity interleukin-2 analogue is R38A or F42K.

16. A method for stimulating the immune system of an animal comprising the following steps:
    (a) preparing a composition comprising lymphokine activated killer cells in accordance with claim 13; and
    (b) administering to the animal a therapeutically effective amount of said lymphokine activated killer cells.

17. The method of claim 16, further defined as a method for treating cancer.

* * * * *